(12) United States Patent
Xu et al.

(10) Patent No.: US 12,303,186 B2
(45) Date of Patent: May 20, 2025

(54) MANUAL CONTROL HANDHELD PRESSURE-ADJUSTABLE IRRIGATION AND SUCTION ELECTROCOAGULATION CUTTER

(71) Applicant: NANJING DRUM TOWER HOSPITAL, Jiangsu (CN)

(72) Inventors: Can Xu, Jiangsu (CN); Dongjin Wang, Jiangsu (CN)

(73) Assignee: NANJING DRUM TOWER HOSPITAL, Jiangsu (CN)

( * ) Notice: Subject to any disclaimer, the term of this patent is extended or adjusted under 35 U.S.C. 154(b) by 0 days.

(21) Appl. No.: 18/850,758

(22) PCT Filed: Apr. 3, 2024

(86) PCT No.: PCT/CN2024/085724
§ 371 (c)(1),
(2) Date: Sep. 25, 2024

(65) Prior Publication Data
US 2025/0134581 A1    May 1, 2025

(30) Foreign Application Priority Data
Oct. 30, 2023  (CN) .......................... 202311416501.3

(51) Int. Cl.
*A61B 18/14*    (2006.01)
*A61B 17/32*    (2006.01)
(Continued)

(52) U.S. Cl.
CPC ...................... *A61B 18/1402* (2013.01); *A61B 2017/320064* (2013.01); *A61B 2018/00208* (2013.01);
(Continued)

(58) Field of Classification Search
CPC ........ A61B 18/1402; A61B 2018/1405; A61B 2018/1432; A61B 2090/0807;
(Continued)

(56) References Cited

U.S. PATENT DOCUMENTS 5,817,121 A * 10/1998 Christoudias ........... A61F 13/38
606/190
2007/0233059 A1 * 10/2007 Christoudias ...... A61B 18/1482
606/45
(Continued)

FOREIGN PATENT DOCUMENTS

CN      110811820 A     2/2020
CN      111419386 A     7/2020
(Continued)

*Primary Examiner* — Nathan R Price
*Assistant Examiner* — Mark A Igel
(74) *Attorney, Agent, or Firm* — MUNCY, GEISSLER, OLDS & LOWE, P.C.

(57) ABSTRACT

The present invention relates to the technical field of electrocoagulation cutters, and in particular, to a manual control handheld pressure-adjustable irrigation and suction electrocoagulation cutter, including: a connecting rod, wherein an irrigation channel and a suction channel which are spaced apart from each other are formed in the connecting rod; a cutting head is arranged at a left end of the connecting rod; a suction port communicated to the suction channel is provided on the cutting head; a head end of the irrigation channel penetrates through the left end of the connecting rod; a connecting head is arranged at a right end of the connecting rod; a mechanical conveying mechanism configured to convey tissue debris cut by the electrocoagulation cutter from a tail end of the suction channel to a middle way of the connecting head is arranged on the connecting rod; an irrigation joint and a suction joint are respectively arranged at front and rear ways of the connecting head; a partition block configured to partition the front way of the connecting (Continued)

head from the other two ways is arranged in the connecting head; an adjustment valve communicated to a tail end of the irrigation channel is arranged in the middle of the connecting rod; and a conveying pipe is arranged between the adjustment valve and the front way of the connecting head. The present invention provides an electrocoagulation cutter capable of avoiding pipeline blockage and good cleaning effect.

9 Claims, 9 Drawing Sheets

(51) Int. Cl.
    *A61B 18/00*     (2006.01)
    *A61B 90/00*     (2016.01)
(52) U.S. Cl.
    CPC ............... *A61B 2018/00607* (2013.01); *A61B 2018/00744* (2013.01); *A61B 2018/0091* (2013.01); *A61B 2018/1412* (2013.01); *A61B 2090/0807* (2016.02); *A61B 2218/002* (2013.01); *A61B 2218/007* (2013.01)
(58) Field of Classification Search
    CPC ........... A61B 2018/00208; A61B 2018/00607; A61B 2018/00744; A61B 2018/0091; A61B 2018/1412; A61B 2218/002; A61B 2218/007

See application file for complete search history.

(56) References Cited

U.S. PATENT DOCUMENTS

| | | | |
|---|---|---|---|
| 2019/0059988 A1* | 2/2019 | Davison | A61B 18/1402 |
| 2019/0099209 A1* | 4/2019 | Witt | A61B 18/1402 |
| 2023/0040816 A1* | 2/2023 | Cheng | A61B 18/1492 |
| 2025/0057584 A1* | 2/2025 | Cheng | A61B 18/1206 |

FOREIGN PATENT DOCUMENTS

| | | | | |
|---|---|---|---|---|
| CN | 212308025 U | 1/2021 | | |
| CN | 113729919 A | 12/2021 | | |
| CN | 217660097 U | 10/2022 | | |
| CN | 117204942 A | 12/2023 | | |
| WO | WO-2004098382 A2 * | 11/2004 | ......... | A61B 18/1482 |
| WO | WO-2013033426 A2 * | 3/2013 | ..... | A61B 17/320758 |
| WO | WO-2018119022 A1 * | 6/2018 | ....... | A61B 17/32002 |

* cited by examiner

MANUAL CONTROL HANDHELD PRESSURE-ADJUSTABLE IRRIGATION AND SUCTION ELECTROCOAGULATION CUTTER

TECHNICAL FIELD

The present invention relates to the technical field of electrocoagulation cutters, and in particular to, a manual control handheld pressure-adjustable irrigation and suction electrocoagulation cutter.

BACKGROUND

An electrocoagulation cutter is cutting equipment used in surgical procedures to replace a traditional mechanical scalpel to achieve tissue cutting, coagulation, and the like. The electrocoagulation cutter mainly achieves separation and coagulation of body tissues through high-frequency and high-voltage current generated by an effective electrode.

Chinese patent No. CN217660097U provides a manual control handheld pressure-adjustable irrigation and suction electrocoagulation cutter, including a handle, a plug, a power cable, soft rubber, a button, a push key, a rotating wheel, a functional pipe, a three-way valve, and an electric hook head. The product of the present utility model has a small volume and is convenient to hold and operate. A stepless speed-adjustment suction valve can effectively maintain the balance of aeroperitoneum, ensure that the surgical operation is not affected. The special electric hook head design improves the cutting efficiency. However, during the cutting and separation operations performed on body tissues in a surgery, some body tissues would inevitably fall into tissue fluid of the body and irrigation fluid. There is a risk of tissue blockage in a pipeline when using the existing electrocoagulation cutter for suction. A suction port of the equipment directly sucks the irrigation fluid and the tissue fluid. An improper operation can easily suck tissues and cause injury. In addition, the current electrocoagulation cutter uses the same pipeline for irrigation and suction, and the fluid left on a pipe wall will be irrigated into the body again during the irrigation, causing a poor cleaning effect and easily cause the fluid to be left. Therefore, a manual control handheld pressure-adjustable irrigation and suction electrocoagulation cutter is needed.

SUMMARY

The present invention aims to provide a manual control handheld pressure-adjustable irrigation and suction electrocoagulation cutter, to solve the technical problems in the background section.

To achieve the above objectives, the present invention adopts the following technical solutions:

A manual control handheld pressure-adjustable irrigation and suction electrocoagulation cutter includes: a connecting rod; an irrigation channel and a suction channel which are spaced apart from each other are formed in the connecting rod; a cutting head is arranged at a left end of the connecting rod; a suction port communicated to the suction channel is provided on the cutting head; a head end of the irrigation channel penetrates through the left end of the connecting rod; a connecting head is arranged at a right end of the connecting rod; the connecting head is three-way; a mechanical conveying mechanism configured to convey tissue debris cut by the electrocoagulation cutter from a tail end of the suction channel to a middle way of the connecting head is arranged on the connecting rod; an irrigation joint and a suction joint are respectively arranged at front and rear ways of the connecting head; a partition block configured to partition the front way of the connecting head from the other two ways is arranged in the connecting head; an adjustment valve communicated to a tail end of the irrigation channel is arranged in the middle of the connecting rod; and a conveying pipe is arranged between the adjustment valve and the front way of the connecting head.

Further, the cutting head is a flat ellipsoid, and the cutting head forms an angle of 150° with the connecting rod.

Further, the suction port is provided at a center position of a side curved surface of the cutting head, and an edge of the suction port is rounded and smooth.

Further, a handle is arranged on an outer wall of the connecting rod; the handle wraps an outer side of the handle; the adjustment valve, the connecting head, and the conveying pipe are all wrapped by the handle; the front and rear ways of the connecting head extend to an outer side of the handle; and a control switch is arranged on the handle.

Further, the mechanical conveying mechanism includes: a conveying screw rod and a micro reduction motor; a conveying chamber is provided on a right side of the connecting rod; the conveying chamber is communicated to the suction channel; the conveying screw rod is arranged in the conveying chamber and cooperates with the conveying chamber; the micro reduction motor is fixedly mounted at a right end of the connecting head; a right end of the conveying screw rod is fixedly connected to an output end of the micro reduction motor; the output end of the micro reduction motor penetrates through and is rotationally connected to the connecting head; and a sealing sleeve is arranged at a position of the micro reduction motor that is in contact with the connecting head.

Further, a first anti-falling pattern and a second anti-falling pattern are respectively arranged on outer walls of the irrigation joint and the suction joint; a single circle of texture of the first anti-falling pattern is like a slope; one surface of the first anti-falling pattern facing a liquid inlet of the irrigation joint has a gradient, and one surface facing away from the liquid inlet is perpendicular to the irrigation joint; and the second anti-falling pattern has the same shape as the first anti-falling pattern.

Further, the adjustment valve is a hollow cylindrical shape; a first flow-through hole and a rotating circular hole are respectively provided at two ends; the flow-through hole is communicated to the tail end of the irrigation channel; a semi-circular closing ring is embedded on a left side of an inner chamber of the adjustment valve; an adjustment valve core is rotationally connected to an inner wall of the closing ring; a circular groove is provided in the adjustment valve core; a second flow-through hole is provided at a rear end of the adjustment valve core; two ends of the second flow-through hole are respectively communicated to the circular groove and the first flow-through hole; a flow-through port communicated to the circular groove is provided on a side wall of the adjustment valve core; an angle of an opening of the flow-through port is less than or equal to 180°; a front end of the adjustment valve core is fixedly connected with a knob post; the knob post is hermetically rotationally connected with the rotating circular hole; a front end of the knob post is fixedly connected with an adjustment knob; and a left end of the conveying pipe is communicated to an inner chamber on a right side of the adjustment valve.

Further, the angle of the opening of the flow-through port is 90°.

Further, a first limiting block and a second limiting block are arranged on a center loop of an outer surface of the adjustment valve core; the first limiting block is arranged at an edge position of one side of the flow-through port close to the conveying pipe; the second limiting block is arranged at a position where the first limiting block rotates counterclockwise 90° along an axis of the adjustment valve core and is located on the same horizontal plane as the other side of the flow-through port.

Further, vertical stripes are provided on the adjustment knob.

Compared with the prior art, the present invention has the beneficial effects below 1. The suction port is provided on the cutting head, so that during operation, the cutting head can be placed into irrigation fluid and tissue fluid for suction. When there is a small amount of irrigation fluid and tissue fluid remaining in the body, one surface, not provided with the suction port, of the cutting head can abut against the body tissue and be lightly pressed to make the tissue fluid and cleaning fluid flow towards the surface with the opening, which facilitates more thorough suction of the irrigation fluid and the tissue fluid, and avoids an operation injury caused by the possibility that the suction port directly sucks the body tissue in the operation process.
2. The conveying screw rod is arranged in the connecting rod. When cut tissues are mixed in the irrigation fluid and tissue fluid in the body, the cut tissues enter a suction pipe through the suction port and, during the flowing, the conveying screw rod is driven by the micro reduction motor to rotate. During the rotation, the tissue debris is mechanically conveyed and pushed to the connecting head, thereby preventing the risk of possible blockage caused by the body tissue in the pipeline.
3. The partition block is arranged in the connecting head, the irrigation joint and the suction joint on the connecting head are separated; the conveying pipe is arranged on the handle; and an irrigation pipe and a suction pipe are formed in the connecting rod, so that the irrigation pipe and the suction pipe run independently. This avoids the sharing of a pipeline for irrigation and suction and ensures the cleaning effect.

Numerals in the accompanying drawings: 1: handle; 2: control switch; 3: adjustment knob; 301: knob post; 4: adjustment valve; 401: closing ring; 402: adjustment valve core; 403: first limiting block; 404: second limiting block; 405: flow-through port; 5: connecting rod; 501: irrigation pipe; 502: suction pipe; 6: cutting head; 601: suction port; 7: conveying screw rod; 8: micro reduction motor; 9: connecting head; 901: partition block; 10: irrigation joint; 1001: first anti-falling pattern; 11: suction joint; 1101: second anti-falling pattern; and 12: conveying pipe.

DETAILED DESCRIPTION

The present invention will be further described in detail below with reference to the accompanying drawings and embodiments.

Figure 1:
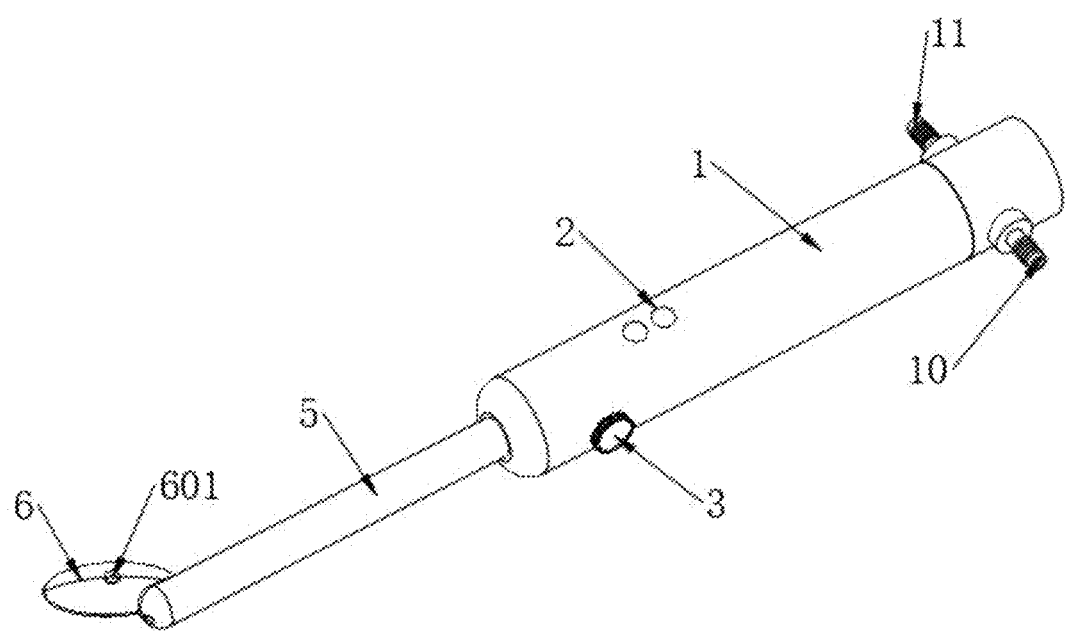
FIG. 1 is a schematic structural diagram of the present invention.
Figure 2:
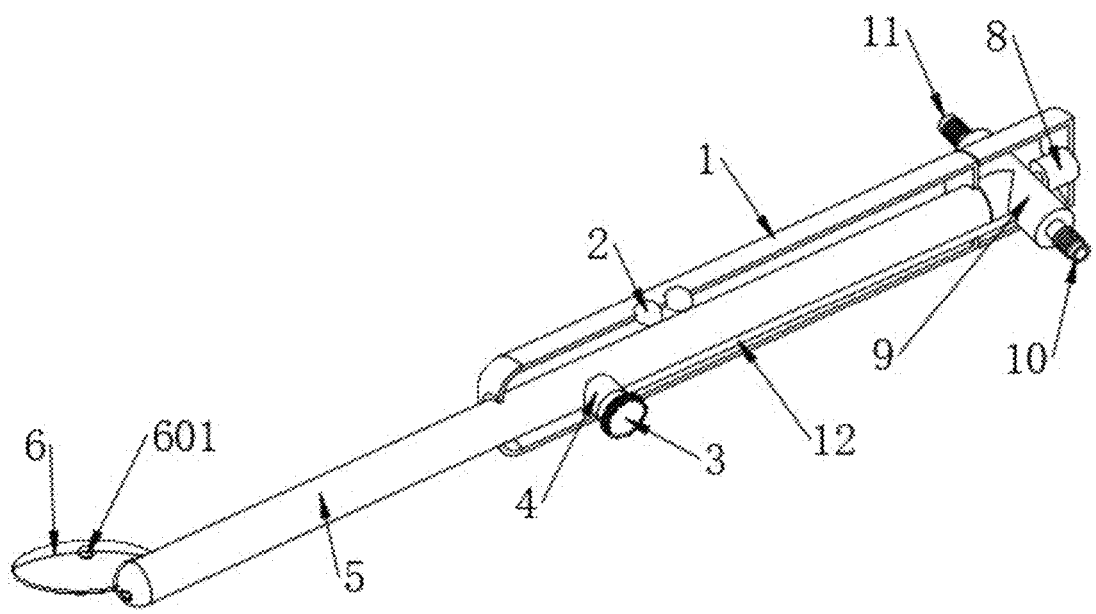
FIG. 2 is a schematic diagram of an internal structure of the present invention.
Figure 3:
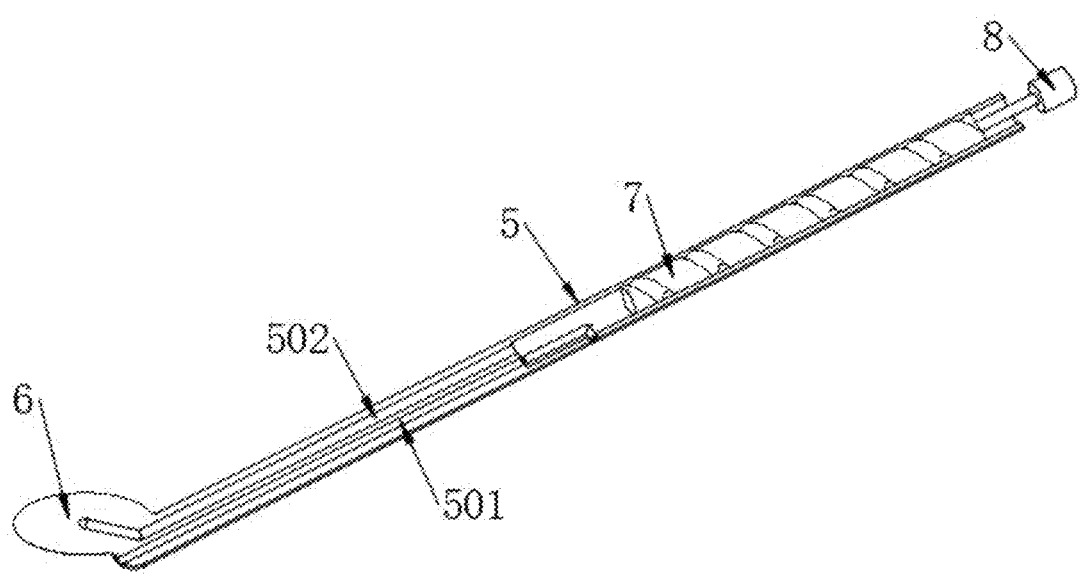
FIG. 3 is a cross-sectional view of a connecting rod in the present invention.
Figure 4:
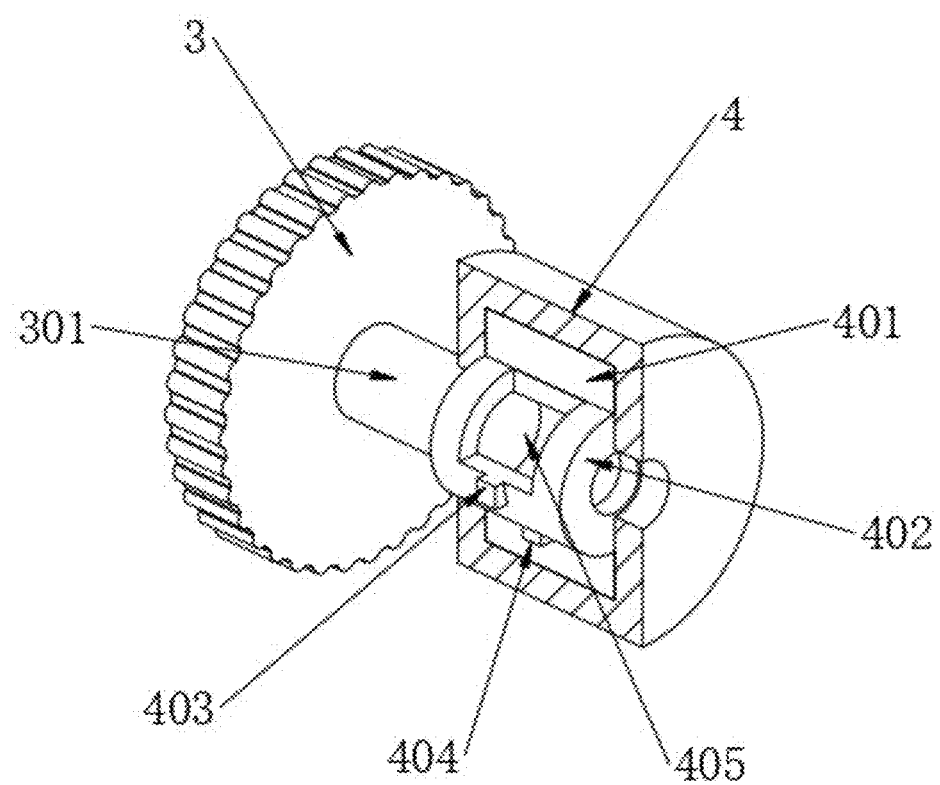
FIG. 4 is a schematic diagram of an adjustment valve core in an opened state in the present invention.
Figure 5:
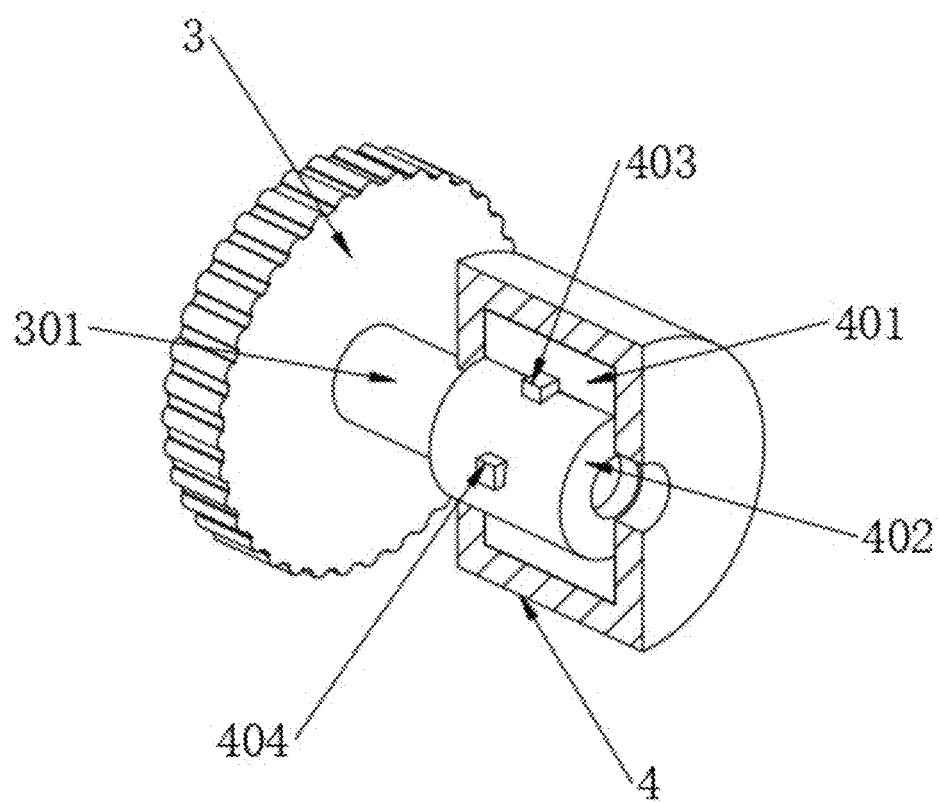
FIG. 5 is a schematic diagram of an adjustment valve core in a closed state in the present invention.
Figure 6:
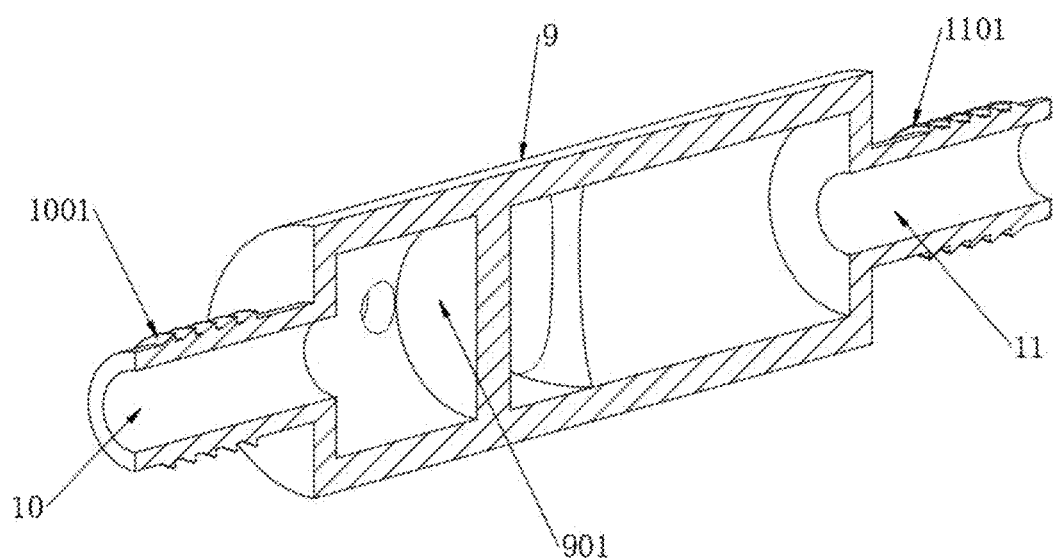
FIG. 6 is a cross-sectional view of a connecting head in the present invention.
Figure 7:
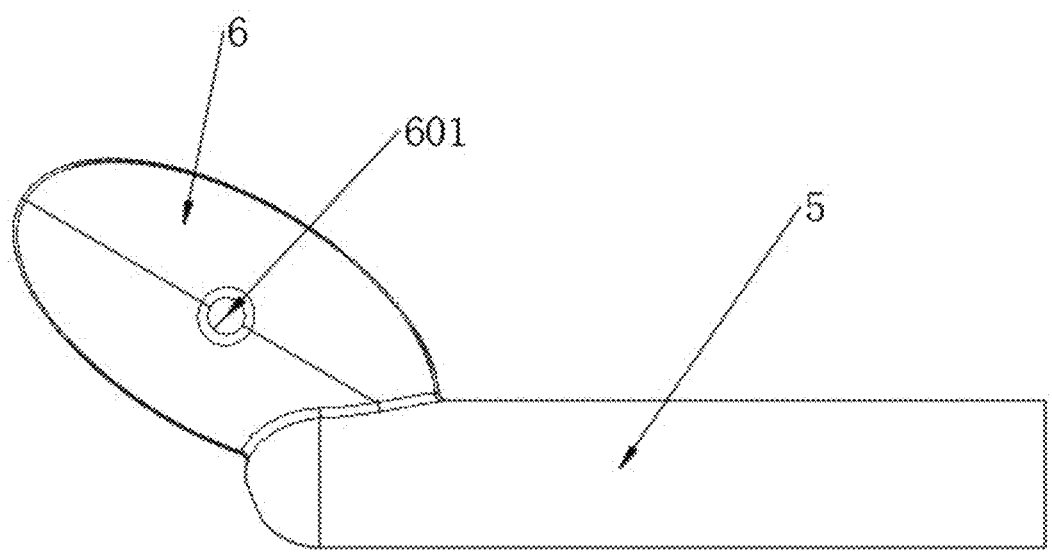
FIG. 7 is a right view of a cutting head in the present invention.
Figure 8:
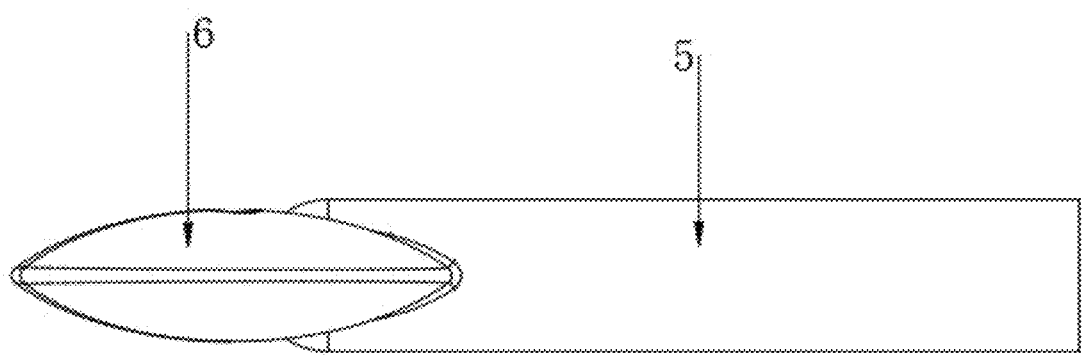
FIG. 8 is a top view of a cutting head in the present invention.
Figure 9:
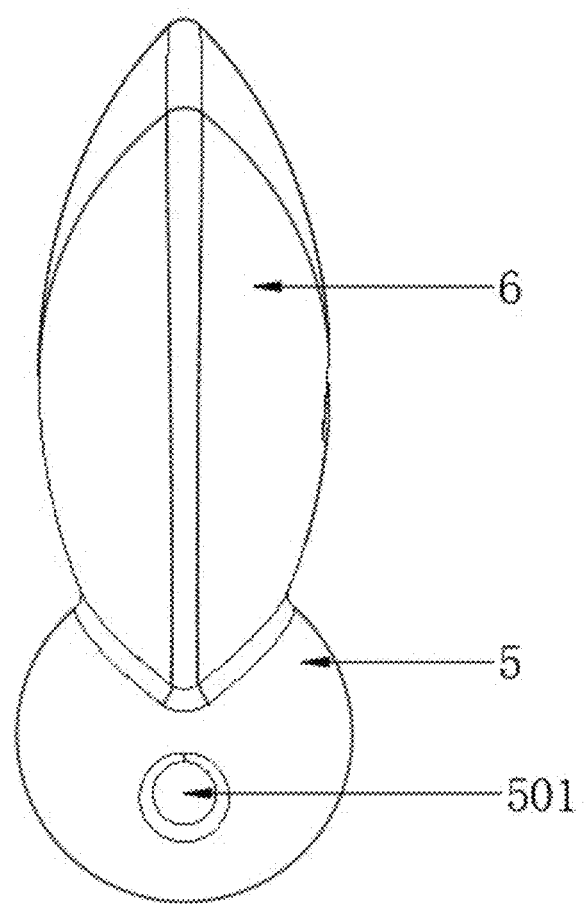
FIG. 9 is a front view of a cutting head in the present invention.

Referring to FIG. 1 to FIG. 9, a manual control handheld pressure-adjustable irrigation and suction electrocoagulation cutter includes: a connecting rod 5; an irrigation channel 501 and a suction channel 502 which are spaced apart from each other are formed in the connecting rod 5; a cutting head 6 is arranged at a left end of the connecting rod 5; a suction port 601 communicated to the suction channel 502 is provided on the cutting head 6; a head end of the irrigation channel 501 penetrates through the left end of the connecting rod 5; a connecting head 9 is arranged at a right end of the connecting rod 5; the connecting head 9 is three-way; a mechanical conveying mechanism configured to convey tissue debris cut by the electrocoagulation cutter from a tail end of the suction channel 502 to a middle way of the connecting head 9 is arranged on the connecting rod 5; an irrigation joint 10 and a suction joint 11 are respectively arranged at front and rear ways of the connecting head 9; a partition block 901 configured to partition the front way of the connecting head 9 from the other two ways is arranged in the connecting head 9; an adjustment valve 4 communicated to a tail end of the irrigation channel 501 is arranged in the middle of the connecting rod 5; and a conveying pipe 12 is arranged between the adjustment valve 4 and the front way of the connecting head 9.

In this embodiment, the cutting head 6 is a flat ellipsoid, and the cutting head 6 forms an angle of 150° with the connecting rod 5. A thinner side surface of the flat ellipsoid-like cutting head 6 is convenient for performing cutting and electrocoagulation on a body tissue; and wide side surfaces on two sides enlarge contact areas with the body, thereby avoiding injury during suction. The cutting head 6 forms the angle of 150° with the connecting rod 5, so that an operator can better operate the cutting head 6 to be in contact with the body tissue in a handheld state.

The suction port 601 is provided at a center position of a side curved surface of the cutting head 6, and an edge of the suction port 601 is rounded and smooth. Providing the suction port 601 at the center position of the cutting head 6 can facilitate the suction operation. Furthermore, if there is a small amount of irrigation fluid and tissue fluid, the cutting head 6 can be operated to form a low point according to the body tissue at a proper position, so as to gather the irrigation fluid and the tissue fluid to the suction port 601.

In this embodiment, a handle 1 is arranged on an outer wall of the connecting rod 5; the handle 1 wraps an outer side of the handle 1; the adjustment valve 4, the connecting head 9, and the conveying pipe 12 are all wrapped by the handle 1; the front and rear ways of the connecting head 9 extend to an outer side of the handle 1; and a control switch 2 is arranged on the handle 1. It is convenient for medical staff to perform a holding operation through the handle 1.

In this embodiment, the mechanical conveying mechanism includes: a conveying screw rod 7 and a micro reduction motor 8; a conveying chamber is provided on a right side of the connecting rod 5; the conveying chamber is communicated to the suction channel 502; the conveying screw rod 7 is arranged in the conveying chamber and cooperates with the conveying chamber; the micro reduction motor 8 is fixedly mounted at a right end of the connecting head 9; a right end of the conveying screw rod 7 is fixedly connected to an output end of the micro reduction motor 8; the output end of the micro reduction motor 8 penetrates through and is rotationally connected to the connecting head 9; and a sealing sleeve is arranged at a position of the micro reduction motor 8 that is in contact with the connecting head 9. The sealing sleeve is arranged at a penetrating point, which can ensure that the micro reduction motor 8 freely rotates in the process of driving the conveying screw rod 7 to rotate, and a sealing state of the penetrating point is maintained to prevent liquid leakage.

In this embodiment, a first anti-falling pattern 1001 and a second anti-falling pattern 1101 are respectively arranged on outer walls of the irrigation joint 10 and the suction joint 11; a single circle of texture of the first anti-falling pattern 1001 is like a slope; one surface of the first anti-falling pattern 1001 facing a liquid inlet of the irrigation joint 10 has a gradient, and one surface facing away from the liquid inlet is perpendicular to the irrigation joint 10; and the second anti-falling pattern 1101 has the same shape as the first anti-falling pattern 1001. By the arrangement of the first anti-falling pattern 1001 and the second anti-falling pattern 1101 on the irrigation joint 10 and the suction joint 11 and the arrangement of the gradient, it is convenient to insert the irrigation joint 10 and the suction joint 11 into externally connected pipelines. Meanwhile, when the equipment works, the externally connected pipelines can be effectively prevented from falling off.

In this embodiment, the adjustment valve 4 is a hollow cylindrical shape; a first flow-through hole and a rotating circular hole are respectively provided at two ends; the flow-through hole is communicated to the tail end of the irrigation channel 501; a semi-circular closing ring 401 is embedded on a left side of an inner chamber of the adjustment valve 4; an adjustment valve core 402 is rotationally connected to an inner wall of the closing ring 401; a circular groove is provided in the adjustment valve core 402; a second flow-through hole is provided at a rear end of the adjustment valve core 402; two ends of the second flow-through hole are respectively communicated to the circular groove and the first flow-through hole; a flow-through port 405 communicated to the circular groove is provided on a side wall of the adjustment valve core 402; an angle of an opening of the flow-through port 405 is less than or equal to 90°; a front end of the adjustment valve core 402 is fixedly connected with a knob post 301; the knob post 301 is hermetically rotationally connected with the rotating circular hole; and a front end of the knob post 301 is fixedly connected with an adjustment knob 3. Vertical stripes are provided on the adjustment knob 3, so that an operator can more stably adjust and rotate the adjustment knob 3 during use, to avoid slippage of the hand contaminated by the tissue fluid. A left end of the conveying pipe 12 is communicated to an inner chamber on a right side of the adjustment valve 4. A first limiting block 403 and a second limiting block 404 are arranged on a center loop of an outer surface of the adjustment valve core 402; the first limiting block 403 is arranged at an edge position of one side of the flow-through port 405 close to the conveying pipe 12; the second limiting block 404 is arranged at a position where the first limiting block 403 rotates counterclockwise 90° along an axis of the adjustment valve core 402 and is located on the same horizontal plane as the other side of the flow-through port 405. During the rotation of the adjustment valve core 402, the adjustment valve core 402 and the closing ring 401 are gradually misplaced, and the adjustment valve core 402 gradually enlarges the contact area with the liquid inside the adjustment valve 4, so as to achieve stepless adjustment of the flow rate of the liquid, thus controlling a water output of the tail end of the irrigation channel 501, so as to facilitate adjustment and irrigation as required. By the arrangement of the first limiting block 403 and the second limiting block 404 on the adjustment valve core 402, it is possible to cooperate with the flow-through port 405 at a 90° for flow rate control and provide control perception for an operator. When the first limiting block 403 is in contact with the closing ring 401, the flow-through port 405 is completely blocked by the closing ring 401, so that the irrigation flow rate is 0. When the adjustment knob 3 drives the adjustment valve core 402 to rotate and the second limiting block 404 is in contact with the closing ring 401, the flow-through port 405 is completely exposed, so that the irrigation flow rate is maximum. The adjustment valve core 402 and the adjustment knob 3 can only rotate within a set range of 90° to avoid excessive operation.

Working principle: In actual use, the irrigation joint 10 and the suction joint 11 are connected to connecting pipes for irrigation and suction. The first anti-falling pattern 1001 and the second anti-falling pattern 1101 will effectively prevent the connecting pipes from falling off. The cutter is connected to a power supply, and a user controls the cutting head 6 by holding the handle 1 to control the connecting rod 5. In the cutting process, when the body tissue needs to be irrigated, when a user turns on the control switch 2, irrigation equipment applies pressure to the connecting pipes and is in a standby state. The adjustment knob 3 is rotated, and the adjustment knob 3 drives the knob post 301 to rotate. The knob post drives the adjustment valve core 402 to rotate. During the rotation of the adjustment valve core 402, the flow-through port 405 is exposed out of the closing ring 401, and the irrigation equipment works. The irrigation fluid enters the irrigation joint 10 and the connecting head 9 through an irrigation equipment pipeline, then enters the adjustment valve 4 through the conveying pipe 12, enters the irrigation channel 501 through the flow-through port 405, and is finally sprayed from the front end of the irrigation channel 501 to irrigate a position to be irrigated. As the adjustment valve core 402 driven by the adjustment knob 3 rotates, the opening of the flow-through port 405 gradually increases, and the flow rate of the irrigation fluid gradually increases. When the second limiting block 404 presses against the closing ring 401, the adjustment knob 3 cannot rotate in the current direction and the opening of the flow-through port 405 reaches its maximum. After the irrigation is completed, the adjustment knob 3 is rotated counterclockwise. The adjustment knob 3 drives the adjustment valve core 402 to turn to an initial position through the knob post 301, and finally causes the first limiting block 403 to touch the closing ring 401. The flow-through port 405 is blocked and closed by the closing ring 401, the irrigation stops. When it is necessary to clear away the irrigation fluid and the tissue fluid in the body, the cutting head 6 is immersed in the fluid. Suction equipment and the micro reduction motor 8 are turned on. A pipeline connected to the suction equipment is pumped to generate negative pressure. The fluid is sucked from the suction port 601 into a suction pipe 502, then enters the connecting head 9 through a thread of the conveying screw rod 7, and finally flows into the suction equipment through the connecting head 9 and the suction joint 11.

Meanwhile, the micro reduction motor 8 drives the conveying screw rod 7 to rotate through the output end. During the rotation of the conveying screw rod 7, the body tissue mixed in the sucked irrigation fluid and tissue fluid is mechanically conveyed, so that the body tissue enters the connecting head 9 under the dual effects of the suction negative pressure and mechanical pushing and is ultimately be sucked by the suction equipment. When the irrigation fluid and the tissue fluid which remain in the body cannot immerse the cutting head 6, the other surface opposite to the suction port 601 abuts against a proper position of the body tissue and is pressed appropriately. The irrigation fluid and tissue fluid left in the body are gathered on the cutting head 6 and are finally sucked and collected by the suction equipment through the suction port 601.

In the description of the present invention, it should be noted that orientations or positional relationships indicated by the terms "upper", "lower", "left", "right", "inner", "outer", "top/bottom end", and the like are orientations or positional relationships as shown in the drawings, and are only for the purpose of facilitating and simplifying the description of the present invention instead of indicating or implying that devices or elements indicated needs to have particular orientations, and be constructed and operated in the particular orientations, so that these terms are not construed as limiting the present invention.

The above only describes the preferred embodiments of the present invention and does not impose any form limitation on the present invention, any simple modifications, equivalent changes, improvements, and the like made by any person skilled in the art to the above embodiments based on the technical essence of the present invention without departing from the scope of the technical solutions of the present invention still fall within the protection scope of the technical solutions of the present invention.

What is claimed is:

1. A manual control handheld pressure-adjustable irrigation and suction electrocoagulation cutter, comprising: a connecting rod (5), wherein an irrigation channel (501) and a suction channel (502) which are spaced apart from each other are formed in the connecting rod (5); a cutting head (6) is arranged at a left end of the connecting rod (5); a suction port (601) communicated to the suction channel (502) is provided on the cutting head (6); a head end of the irrigation channel (501) penetrates through the left end of the connecting rod (5); a connecting head (9) is arranged at a right end of the connecting rod (5); the connecting head (9) is three-way; a mechanical conveying mechanism configured to convey tissue debris cut by the electrocoagulation cutter from a tail end of the suction channel (502) to a middle way of the connecting head (9) is arranged on the connecting rod (5); an irrigation joint (10) and a suction joint (11) are respectively arranged at front and rear ways of the connecting head (9); a partition block (901) configured to partition the front way of the connecting head from the other two ways is arranged in the connecting head (9); an adjustment valve (4) communicated to a tail end of the irrigation channel (501) is arranged in the middle of the connecting rod (5); a conveying pipe (12) is arranged between the adjustment valve (4) and the front way of the connecting head (9);

the mechanical conveying mechanism comprises; a conveying screw rod (7) and a micro reduction motor (8); a conveying chamber is provided on a right side of the connecting rod (5); the conveying chamber is communicated to the suction channel (502); the conveying screw rod (7) is arranged in the conveying chamber and cooperates with the conveying chamber; the micro reduction motor (8) is fixedly mounted at a right end of the connecting head (9); a right end of the conveying screw rod (7) is fixedly connected to an output end of the micro reduction motor (8); the output end of the micro reduction motor (8) penetrates through and is rotationally connected to the connecting head (9); and a sealing sleeve is arranged at a position of the micro reduction motor (8) that is in contact with the connecting head (9).

2. The manual control handheld pressure-adjustable irrigation and suction electrocoagulation cutter according to claim 1, wherein the cutting head (6) is a flat ellipsoid, and the cutting head (6) forms an angle of 150° with the connecting rod (5).

3. The manual control handheld pressure-adjustable irrigation and suction electrocoagulation cutter according to claim 2, wherein the suction port (601) is provided at a center position of a side curved surface of the cutting head (6), and an edge of the suction port (601) is rounded and smooth.

4. The manual control handheld pressure-adjustable irrigation and suction electrocoagulation cutter according to claim 1, wherein a handle (1) is arranged on an outer wall of the connecting rod (5); the adjustment valve (4), the connecting head (9), and the conveying pipe (12) are all wrapped by the handle (1); the front and rear ways of the connecting head (9) extend to an outer side of the handle (1); and a control switch (2) is arranged on the handle (1).

5. The manual control handheld pressure-adjustable irrigation and suction electrocoagulation cutter according to claim 1, wherein a first anti-falling pattern (1001) and a second anti-falling pattern (1101) are respectively arranged on outer walls of the irrigation joint (10) and the suction joint (11); a single circle of texture of the first anti-falling pattern (1001) is like a slope; one surface of the first anti-falling pattern (1001) facing a liquid inlet of the irrigation joint (10) has a gradient, and one surface facing away from the liquid inlet is perpendicular to the irrigation joint (10); and the second anti-falling pattern (1101) has the same shape as the first anti-falling pattern (1001).

6. The manual control handheld pressure-adjustable irrigation and suction electrocoagulation cutter according to claim 1, wherein the adjustment valve (4) is a hollow cylindrical shape; a first flow-through hole and a rotating circular hole are respectively provided at two ends; the flow-through hole is communicated to the tail end of the irrigation channel (501); a semi-circular closing ring (401) is embedded on a left side of an inner chamber of the adjustment valve (4); an adjustment valve core (402) is rotationally connected to an inner wall of the closing ring (401); a circular groove is provided in the adjustment valve core (402); a second flow-through hole is provided at a rear end of the adjustment valve core (402); two ends of the second flow-through hole are respectively communicated to the circular groove and the first flow-through hole; a flow-through port (405) communicated to the circular groove is provided on a side wall of the adjustment valve core (402); an angle of an opening of the flow-through port (405) is less than or equal to 180°; a front end of the adjustment valve core (402) is fixedly connected with a knob post (301); the knob post (301) is hermetically rotationally connected with the rotating circular hole; a front end of the knob post (301) is fixedly connected with an adjustment knob (3); and a left end of the conveying pipe (12) is communicated to an inner chamber on a right side of the adjustment valve (4).

7. The manual control handheld pressure-adjustable irrigation and suction electrocoagulation cutter according to claim 6, wherein the angle of the opening of the flow-through port (405) is 90°.

8. The manual control handheld pressure-adjustable irrigation and suction electrocoagulation cutter according to claim 7, wherein a first limiting block (403) and a second limiting block (404) are arranged on a center loop of an outer surface of the adjustment valve core (402); the first limiting block (403) is arranged at an edge position of one side of the flow-through port (405) close to the conveying pipe (12); the second limiting block (404) is arranged at a position where the first limiting block (403) rotates counterclockwise 90° along an axis of the adjustment valve core (402) and is located on the same horizontal plane as the other side of the flow-through port (405).

9. The manual control handheld pressure-adjustable irrigation and suction electrocoagulation cutter according to claim 6, wherein vertical stripes are provided on the adjustment knob (3).

* * * * *